US009766251B2

(12) United States Patent
Essig et al.

(10) Patent No.: US 9,766,251 B2
(45) Date of Patent: Sep. 19, 2017

(54) ANTI-HUMAN IGG1 ANTIBODY

(71) Applicant: Hoffmann-La Roche Inc., Nutley, NJ (US)

(72) Inventors: Ulrich Essig, Planegg (DE); Stefan Klostermann, Neuried (DE); Frank Kowalewsky, Munich (DE); Kay-Gunnar Stubenrauch, Penzberg (DE); Rudolf Vogel, Weilheim (DE); Uwe Wessels, Penzberg (DE)

(73) Assignee: HOFFMANN-LA ROCHE INC., Nutley, NJ (US)

( * ) Notice: Subject to any disclaimer, the term of this patent is extended or adjusted under 35 U.S.C. 154(b) by 0 days.

(21) Appl. No.: 14/627,782

(22) Filed: Feb. 20, 2015

(65) Prior Publication Data
US 2015/0323543 A1 Nov. 12, 2015

Related U.S. Application Data

(63) Continuation of application No. 13/769,153, filed on Feb. 15, 2013, now abandoned, which is a continuation of application No. PCT/EP2011/063906, filed on Aug. 12, 2011.

(30) Foreign Application Priority Data

Aug. 17, 2010 (EP) ..................... 10173090

(51) Int. Cl.
*G01N 33/68* (2006.01)
*C07K 16/42* (2006.01)

(52) U.S. Cl.
CPC ....... *G01N 33/686* (2013.01); *C07K 16/4241* (2013.01); *C07K 16/4283* (2013.01); *G01N 33/6854* (2013.01); *C07K 2317/14* (2013.01); *C07K 2317/30* (2013.01); *C07K 2317/33* (2013.01); *C07K 2317/54* (2013.01); *C07K 2317/92* (2013.01)

(58) Field of Classification Search
CPC ............. G01N 33/6854; G01N 33/686; C07K 16/4241; C07K 16/4283; C07K 2317/14; C07K 2317/30; C07K 2317/33; C07K 2317/54; C07K 2317/92
See application file for complete search history.

(56) References Cited

U.S. PATENT DOCUMENTS

| 4,816,567 A | 3/1989 | Cabilly et al. |
|---|---|---|
| 4,925,787 A | 5/1990 | Tanihara et al. |
| 5,202,238 A | 4/1993 | Fell et al. |
| 5,204,244 A | 4/1993 | Fell et al. |
| 5,332,665 A | 7/1994 | Reed et al. |
| 5,636,137 A | 6/1997 | Hazelden |
| 5,736,137 A * | 4/1998 | Anderson et al. ......... 424/133.1 |
| 5,821,337 A | 10/1998 | Carter et al. |
| 6,525,174 B1 | 2/2003 | Young et al. |
| 7,008,796 B2 | 3/2006 | Wohlstadter et al. |
| 2003/0068664 A1 | 4/2003 | Albitar et al. |
| 2004/0214761 A1 | 10/2004 | Raison et al. |
| 2005/0169925 A1 | 8/2005 | Bardroff et al. |
| 2005/0226876 A1 | 10/2005 | Graus et al. |
| 2008/0102474 A1 | 5/2008 | Lenz et al. |
| 2012/0208216 A1 | 8/2012 | Essig et al. |

FOREIGN PATENT DOCUMENTS

| EP | 0061888 A2 | 10/1982 |
|---|---|---|
| EP | 1 098 198 | 5/2001 |
| JP | 2004191382 A | 7/2004 |
| WO | WO93/21319 | 10/1993 |
| WO | 98/04281 | 2/1998 |
| WO | 03/070760 | 8/2003 |
| WO | 2004/087756 A2 | 10/2004 |
| WO | 2004/096274 A1 | 11/2004 |
| WO | 2005/005635 A2 | 1/2005 |
| WO | 2005/023872 A1 | 3/2005 |
| WO | 2005/100402 A1 | 10/2005 |
| WO | 2005/108989 A2 | 11/2005 |
| WO | 2006/066912 A2 | 6/2006 |
| WO | 2006/072564 A1 | 7/2006 |
| WO | 2008/031532 A1 | 3/2008 |
| WO | 2011/048043 A1 | 4/2011 |
| WO | 2012/022682 A1 | 2/2012 |

OTHER PUBLICATIONS

Abe et al., 1993. Production and immunodiagnostic applications of antihuman light chain monoclonal antibodies. American J. Clinical Pathology 100: 67-74.*
Bourdage et al., 2005. Effect of double antigen bridging immunoassay format on antigen coating concentration dependence and implications for designing immunogenicity assays for monoclonal antibodies. J. Pharmaceut. Biomed. Anal. 39: 685-690.*
Van Schouwenburg et al., 2010. A novel method for the detection of antibodies to adalimumab in the presence of drug reveals "hidden" immunogenicity in rheumatoid arthritis patients. Immunological Meth. 362: 82-88.*
Apathy et al., "A sensitive immunoradiometric assay for the quantification of murine monoclonal antibodies in human serum" J Pharm Biomed Anal. 7(5):593-600 ( 1989).
Asada et al., "Molecular evolution of IgG subclass among nonhuman primates: implication of differences in antigenic determinants among Apes" Primates 43(4):343-9 (Oct. 2002).
Benincosa et al., "Pharmacokinetics and pharmacodynamics of a humanized monoclonal antibody to factor IX in cynomolgus monkeys" J Pharmacol Exp Ther. 292(2):810-6 (Feb. 2000).
Black et al., "Cross-reactivity of 75 monoclonal antibodies to human immunoglobulin with sera of non-human primates" Immunol Lett. 37:207-13 (Aug. 1993).
Bruck et al., "Purification of mouse monoclonal antibodies from ascitic fluid by DEAE Affi-Gel Blue chromatography" Methods in Enzymology 121:587-596 (1986).
Calvas et al., "Characterization of the Three Immunoglobulin G Subclasses of Macaques" Scandinavian Journal of Immunology 49(6):595-610 (Jun. 1999).
Chevrier et al., "Sensitive Detection of Human IgG in ELISA Using a Monoclonal Anti-IgG-Peroxide Conjugate" Hybridoma and Hybridomics 23(6):362-367 ( 2004).

(Continued)

*Primary Examiner* — Christine Foster
*Assistant Examiner* — Ellen J Marcsisin
(74) *Attorney, Agent, or Firm* — James E. Nesbitt

(57) ABSTRACT

Herein are reported a monoclonal antibody specifically binding to a human IgG1 antibody and not specifically binding to the immunoglobulin of an experimental animal and the use of the antibody in immunoassays.

26 Claims, 4 Drawing Sheets

(56) References Cited

OTHER PUBLICATIONS

Chothia et al., "Canonical structures for the hypervariable regions of immunoglobulins" J Mol Biol 196(4):901-917 ( 1987).

Clackson et al., "Making antibody fragments using phage display libraries" Nature 352:624-628 (Aug. 15, 1991).

International Search Report and Written Opinion for International Patent Application No. PCT/EP2011/063906 (Dec. 9, 2011).

Damen et al., "Bioanalytical methods for the quantification of therapeutic monoclonal antibodies and their application in clinical pharmacokinetic studies" Human Antibodies 18:47-73 (2009).

Galfre, G. et al., "Preparation of Monoclonal Antibodies: Strategies and Procedures" Methods in Enzymology 73:3-46 ( 1981).

Hamilton et al., "Epitope mapping of human immunoglobulin-specific murine monoclonal antibodies with domain-switched, deleted and point-mutated chimeric antibodies" J Immunol Methods 158(1):107-22 (Jan. 1993).

Hansen et al., "An ELISA for quantification of murine IgG in rat plasma: application to the pharmacokinetic characterization of AP-3, a murine anti-glycoprotein IIIa monoclonal antibody, in the rat" J Pharm Biomed Anal. 21(5):1011-6 (Dec. 1999).

Hazlewood et al., "The acquisition of anti-pneumococcal capsular polysaccharide Haemophilus influenzae type b and tetanus toxoid antibodies, with age, in the UK" Clin Exp Immunol. 93(2):157-64 (Aug. 1993).

He et al., "Humanization and Pharmacokinetics of a monoclonal antibody with specificity for both E- and P-Selectin" The Journal of Immunology 160:1029-1035 (1998).

Hinton et al., "Engineered human IgG antibodies with longer serum half-lives in primates" J Biol Chem 279(8):6213-6216 (Feb. 20, 2004).

Hosoi et al., "Monoclonal anti-human IgG antibodies for quantitation of allergen-specific IgG in human sera" J Allergy Clin Immunol. 75(2):320-7 (Feb. 1985).

Iborra et al., "Vaccination with a plasmid DNA cocktail encoding the nucleosomal histones of Leishmania confers protection against murine cutaneous leishmaniosis" Vaccine 22(29-30):3865-76 (Sep. 28, 2004).

Jacobsen et al., "Molecular and Functional Characterization of Cynomolgus Monkey IgG Subclasses" J Immunol. 186:341-9 (Dec. 3, 2011).

Jefferis et al., "Evaluation of monoclonal antibodies having specificity for human IgG subclasses: results of an IUIS/WHO collaborative study" Immunology Letters, Elsevier 10(3-4):223-252 (1985).

Jefferis et al., "Evaluation of monoclonal antibodies having specificity for human IgG subclasses: results of the 2nd IUIS/WHO collaborative study" Immunology Letters, Elsevier 31(2):143-168 (Feb. 1, 1992).

Jose et al., "Immunogenic and antigenic epitopes of immunoglobulin—XX. Denaturation of human IgG3 by free radicals" Mol Immunol. 24(11):1145-50 (Nov. 1987).

Kageyama et al., "Pharmacokinetics and pharmacodynamics of AJW200, a humanized monoclonal antibody to von Willebrand factor, in monkeys" Arterioscler Thromb Vasc Biol. 22(1):187-92 (Jan. 2002).

Koehler, G., et al., "Continuous cultures of fused cells secreting antibody of predefined specificity" Nature 256:495-497 (Aug. 7, 1975).

Lei et al., "Human melanoma-associated retinopathy (MAR) antibodies alter the retinal ON-response of the monkey ERG in vivo" Invest Ophthalmol Vis Sci. 41(1):262-6 (Jan. 2000).

Lewis et al., "Cloning and sequence analysis of κ and γ cynomolgus monkey immunoglobulin cDNAs" Developmental & Comparative Immunology 17(6):549-56 (1993).

Lonberg, "Human antibodies from transgenic animals" Nat Biotechnol 23(9):1117-1125 (Sep. 2005).

Lü et al., "oncentration of IgG in the sera of normal rhesus macaques as determined by a species-specific radial immunodiffusion assay" J Immunol Methods 197(1-2):193-6 (Oct. 1996).

Marks et al., "By-passing immunization, human antibodies from V-gene libraries displayed on phage" J Mol Biol 222:581-597 ( 1991).

Morrison et al., "Chimeric human antibody molecules: Mouse antigen-binding domains with human constant region domains" P Natl Acad Sci USA 81:6851-6855 (Nov. 1984).

Nath et al., "The amino-terminal immunoglobulin-like domain of sialoadhesin contains the sialic acid binding site. Comparison with CD22" J Biol Chem. 270(44 SUPPL :26184-91) (Nov. 1995).

Neuberger et al., "A hapten-specific chimaeric IgE antibody with human physiological effector function" Nature 314:268-270 (Mar. 21, 1985).

Paul Carter et al., "Humanization of an anti-p185 HER2 antibody for human cancer therapy" Proc. Natl. Acad. Sci USA 89:4285-4289 (May 1992).

Peter T. Jones et al., "Replacing the complementarity-determining regions in a human antibody with those from a mouse" Nature Publishing Group 321:522-525 (May 29, 1986).

Presta et al., "Humanization of an Antibody Directed Against IgE" J Immunol 151(5):2623-2632 (Sep. 1, 1993).

Presta, L., "Antibody engineering" Curr Opin Struc Biol 2:593-596 ( 1992).

Reichmann et al., "Reshaping human antibodies for therapy" Nature 332:323-327 (Mar. 24, 1988).

Santora et al., "Characterization of Noncovalent Complexes of Recombinant Human Monoclonal Antibody and Antigen Using Cation Exchange, Size Exclusion Chromatography and BIAcore" Analytical Biochemistry 299:119-129 (2001).

Sims et al., "A Humanized CD18 Antibody Can Block Function Without Cell Destruction" J Immunol 151(4):2296-2308 (Aug. 15, 1993).

Stephens et al., "Comprehensive pharmacokinetics of a humanized antibody and analysis of residual anti-idiotypic responses" Immunology 85(4):668-74 (Aug. 1995).

Stubenrauch, K. et al., "Evaluation of an immunoassay for human-specific quantitation of therapeutic antibodies in serum samples from non-human primates" J. of Pharmaceutical and Biomedical Analysis 49:1003-1008 ( 2009).

Tang et al., "Cloning and characterization of cDNAs encoding four different canine immunoglobulin γ chains" Veterinary Immunology and Immunopathology 80(3-4):259-270 (Aug. 2001).

Van Der Merwe et al., "CD80 (B7-1) binds both CD28 and CTLA-4 with a low affinity and very fast kinetics" J Exp Med. 185(3):393-403 ( 1997).

Verhoeyen et al., "Reshaping human antibodies: Grafting an antilysozyme activity" Science 239:1534-1536 (Mar. 1988).

Webarchive—Antibodies (anti-Human and others as indicated), (1997).

Berzofsky et al. Immunology: In 3 Volumes. W. Paul, Moscow:Mir, vol. 3:270 ( 1987-1989).

Schildbach et al., "Altered Hapten Recognition by Two Anti-digoxin Hybridoma Variants Due to Variable Region Point Mutations" The Journal of Biological Chemistry 266(7):4640-4647 (Mar. 1991).

Aonymous Internet Article 998 XP002337723, Human Immunoglobulin IgG (fc) chain antibodies from Research Diagnostics Inc, (2 pages).

Anonymous version 2 Antibodies Internet Article 1998, RDI homepage, (2 pages).

Anonymous, ECL Product Specification: 'Anti-human IgG, peroxidase-linked species-specific whole antibody (from sheep) NA 933' 1998, XP002608617 Retrieved from the internet: URL: http://www.gelifesciences.com/aptrix/upp00919.nsf/Content/47729A1564E1AB55C1257628001CC069/$file/na933ps.pdf, ( 4 pages).

Baturin et al., "Development of a Russian immuno-enzyme test system for determining allergenspecific IgE and IgG antibodies for diagnosis of mycoses" Meditsinskaya Immunologiya 9(2-3):336-343 (2007).

Campbell, Laboratory Techniques in Biochemistry and Mol. Biol. Burdon et al., Amsterdam Elsevier Science Publishers, vol. 13 (1985), Contents, (10 pages).

(56) References Cited

OTHER PUBLICATIONS

Dunstan et al., "Erythrocyte antigens on human platelets. Absence of Rh, Duffy, Kell, Kidd, and Lutheran antigens" Transfusion 24(3):243-6 (1984).
Hamilton et al., "Monoclonal antibody-based immunoenzymetric assays for quantification of human IgG and its four subclasses" J Immunoassay 9(3-4):275-96 (1988).
Harlow et al. Antibodies: A Laboratory Manual Cold Spring Harbor, NY: Cold Spring Harbor Laboratory Press,,:141-142 (1988).
Jefferis, "Human IgG subclass-specific epitopes recognised by murine monoclonal antibodies" Monogr Allergy. 20:26-33 (1986).
Riechmann et al., "Reshaping Human Antibodies for Therapy" Nature 332(24):323-327 (Mar. 24, 1988).
Serotec—Excerpt from the Serotec catalogue from 1995, (1 page).
Sigma—Pages from Sigma catalogue, pp. 1036-1045 (6 pages) (2002-2003).

* cited by examiner

SEQUENCE LISTING

```
<160> NUMBER OF SEQ ID NOS: 4

<210> SEQ ID NO 1
<211> LENGTH: 330
<212> TYPE: PRT
<213> ORGANISM: Homo sapiens

<400> SEQUENCE: 1

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
```

```
                    225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 2
<211> LENGTH: 330
<212> TYPE: PRT
<213> ORGANISM: Homo sapiens

<400> SEQUENCE: 2

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270
```

```
Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 3
<211> LENGTH: 330
<212> TYPE: PRT
<213> ORGANISM: Artificial Sequence
<220> FEATURE:
<223> OTHER INFORMATION: IgG1 variant

<400> SEQUENCE: 3

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300
```

-continued

```
Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 4
<211> LENGTH: 98
<212> TYPE: PRT
<213> ORGANISM: Homo sapiens

<400> SEQUENCE: 4

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val
```

ANTI-HUMAN IGG1 ANTIBODY

CROSS REFERENCE TO RELATED APPLICATIONS

This application is a continuation of U.S. patent application Ser. No. 13/769,153, having a filing date of Feb. 15, 2013, which is a continuation of International Application No. PCT/EP2011/063906 having an international filing date of Aug. 12, 2011, the entire contents of which are incorporated herein by reference, and which claims benefit under 35 U.S.C §119 to European Patent Application No. 10173090.1, filed Aug. 17, 2010.

SEQUENCE LISTING

The instant application contains a Sequence Listing submitted via EFS-Web and is hereby incorporated by reference in its entirety. Said ASCII copy, created on Feb. 20, 2015, is named P4659C2SeqList.txt, and is 9,927 bytes in size.

FIELD OF THE INVENTION

Herein are reported antibodies specifically binding to antibodies of human IgG1 class and use thereof.

BACKGROUND OF THE INVENTION

Since the development of the first monoclonal antibodies by Koehler and Milstein in 1974 a lot of efforts have been dedicated to the development of antibodies which are appropriate for therapy in humans. The first monoclonal antibodies which became available had been developed in mice and rats. In the past ten years an ever growing number of human monoclonal antibodies or humanized monoclonal antibodies have reached the market. Well-known examples include for example Herceptin® and MabThera® from F. Hoffmann-La Roche A G, Basel.

A quite significant number of human or humanized monoclonal antibodies is under investigation and needs to be studied in experimental animals, before entry into human can be considered for the first trial purposes. Important criteria like bio-availability and antibody clearance just to mention two of them have to be studied. Many of these studies require the quantification of the therapeutic antibody in the background of the experimental animal's own antibodies. In most cases mammals are used as experimental animals. Toxicology often is first assessed in rodents like mice or rats. In the more advanced stages of drug development, especially before entry of the drug into human beings, even monkeys have to be included into such pre-clinical studies.

Mammals usually have between about 10 to about 30 milligram of antibody per ml in the circulation. Therapeutic monoclonal antibodies typically have to be tested with serum levels ranging from about between 1 nanogram per ml to about 100 microgram per ml. The therapeutic antibody, thus, has to be detected against a background of experimental animal's antibodies which are in an excess of about 100-fold to 10 million-fold.

The detection of a human or humanized therapeutic antibody in the background of an experimental animal's antibody represents quite a significant task to the pharmacologist. The detection of a human or humanized antibody becomes more and more difficult the closer the test animal is related to *H. sapiens*.

In US 2004/214761 a method for treating multiple myeloma is reported. A method for the qualitative and quantitative determination of class IgG human antibodies is reported in EP-A-1 098 198. In WO 2006/066912 the detection of a therapeutic antibody in an experimental animal is reported. An anti-drug antibody assay is reported in WO 2008/031532. In U.S. Pat. No. 5,332,665 species specific, high affinity monoclonal antibodies are reported.

Jefferis, R., et al., report (Immunol. Lett. 31 (1992) 143-168 and Immunol. Lett. 10 (1985) 223-252) the evaluation of monoclonal antibodies having specificity for human IgG subclasses. Human IgG subclass-specific epitopes recognized by murine monoclonal antibodies are reported by Jefferis, R. (Monographs in Allergy, Karger, Basel (CH), 20 (1986) 26-33). Lewis, A. P., et al., report the cloning and sequence analysis of kappa and gamma cynomolgus monkex immunoglobulin cDNA (Dev. Compar. Immunol. 17 (1993) 549-560). Molecular and functional characterization of cynomolgus monkey IgG subclasses is reported by Jacobsen, F. W., et al. (J. Immunol. 186 (2011) 341-349). Calvas, P., et al., (Scand. J. Immunol. 49 (1999) 595-610) report the characterization of three immunoglobulin G subclasses of macaques. The evaluation of an immunoassay for human-specific quantitation of therapeutic antibodies in serum samples from non-human primates is reported by Stubenrauch, K-G., et al. (J. Pharm. Biomed. Analysis 49 (2009) 1003-1008). Liang, T., et al. (Vet. Immunol. Immunopat. 80 (2001) 259-270) report the cloning and characterization of cDNAs encoding four different canine immunoglobulin gamma chains.

SUMMARY OF THE INVENTION

Herein is reported as an aspect an epitope present on human antibodies of the immunoglobulin class IgG1 that is not present on human antibodies of the class IgG2, IgG3 and IgG4. Additionally this epitope is not present on the antibodies of cynomolgus monkeys.

As one aspect herein is reported an antibody specifically binding to antibodies of human IgG1 class and antibodies of chimpanzee IgG class and not specifically binding to antibodies of an experimental animal, such as cynomolgus monkey.

Also an aspect as reported herein is the use of the antibodies as reported herein in an assay.

The antibodies as reported herein can be used e.g. for the determination of a therapeutic antibody of human IgG1 class in the serum of cynomolgus monkeys and rhesus-monkeys.

One aspect the herein reported epitope is characterized in comprising amino acid positions 16, 82, and 97 of SEQ ID NO: 04 (human IgG1 CH1 domain).

Another aspect as reported herein is an antibody that can be obtained from cell line DSM ACC3076 (M-1.19.31). This antibody has a reduced intra-species cross-reactivity e.g. compared to antibody M-R10Z8E9 produced by cell line DSM ACC2708. The antibody binds to a different epitope which is in the Fab-region, is not influenced by a neighboring glycosylation site, and can be used with an antibody selected from antibody M-1.3.2 produced by cell line DSM ACC3006, antibody M-1.5.8 produced by cell line DSM ACC3007, antibody M-1.7.10 produced by cell line DSM ACC3008, and antibody M-R10Z8E9 produced by cell line DSM ACC2708 in an immunoassay for the determination of full length antibodies of human IgG1 class as well as Fab antibodies comprising a human IgG1 CH1 domain as the binding site of each of the antibodies is present only once in these therapeutic antibodies.

One aspect as reported herein is a monoclonal antibody specifically binding to antibodies of human IgG1 class and antibodies of chimpanzee IgG class or Fab fragments thereof. In one embodiment the antibody is a non-human animal derived antibody. In one embodiment the antibody is specifically binding to the heavy chain constant region of an antibody of human IgG1 class. In one embodiment the antibody is specifically binding to the Fab region of an antibody of human IgG1 class. In one embodiment the antibody is specifically binding to the CH1 domain of an antibody of human IgG1 class. In one embodiment the antibody is specifically binding to an antibody of chimpanzees IgG class. In one embodiment the antibody is not specifically binding the antibodies of an experimental animal. In one embodiment the antibody is not specifically binding to cynomolgus monkey antibodies and rhesus-monkey antibodies.

Another aspect as reported herein is a monoclonal antibody obtained from the cell line DSM ACC3076.

Also an aspect as reported herein is an antibody that is specifically binding to the same or an overlapping epitope as the antibody produced by the cell line DSM ACC3076.

An aspect as reported herein is the cell line DSM ACC3076.

Also an aspect as reported herein is the use of an antibody as reported herein in an immunoassay.

A further aspect as reported herein is a kit comprising
a) an antibody obtained from cell line DSM ACC3076,
b) an antibody obtained from cell line DSM ACC2708, or DSM ACC 3006, or DSM ACC3007, or DSM ACC3008.

Also an aspect as reported herein is a method for detecting a therapeutic antibody of human IgG1 class in a sample obtained from an experimental animal comprising the steps of
a) providing the sample to be analyzed,
b) incubating the sample with an antibody as reported herein,
c) optionally incubating the sample with a reagent for the selective detection of total, active, anti-drug antibody (ADA)-bound, or antigen-bound therapeutic antibody, and
d) correlating the complex formed in (b) or (c) to the presence of the therapeutic antibody and thereby detecting the therapeutic antibody.

One aspect as reported herein is a method for determining a therapeutic antibody of human IgG1 class in a sample obtained from an experimental animal using an antigen bridging immunoassay comprising a capture antibody and a tracer antibody, characterized in that the capture antibody and the tracer antibody are both independently selected from antibodies binding to the same epitope as an antibody produced by cell line DSM ACC 3006, or DSM ACC3007, or DSM ACC3008, or DSM ACC3076.

In one embodiment the therapeutic antibody is a Fab fragment comprising a human IgG1 CH1 domain. In one embodiment the experimental animal is selected from the group comprising the members of the families of marmosets and tamarins, old world monkeys, dwarf and mouse lemurs, gibbons and lesser apes, true lemurs, as well as crossings thereof. In one embodiment the experimental animal is a rhesus-monkey, or a marmoset monkey, or a baboon monkey, or a cynomolgus monkey. In one embodiment the experimental animal is a macaca or macaque monkey. In one embodiment the experimental animal is a cynomolgus monkey or a rhesus-monkey.

One aspect as reported herein is the use of an antibody which is specifically binding to a therapeutic antibody of human IgG1 class for determining the concentration of total, active, ADA-bound, or antigen-bound therapeutic antibody in a sample obtained from an experimental animal whereby the antibody is binding to the same epitope as an antibody produced by cell line DSM ACC3006, or DSM ACC3007, or DSM ACC3008, or DSM ACC3076.

One aspect as reported herein is an antibody composition comprising a mixture of the antibody produced by the cell line DSM ACC3006, and/or the cell line DSM ACC2708, and/or the cell line DSM ACC3007, and/or the cell line DSM ACC3008, and/or the cell line DSM ACC3076.

One aspect as reported herein is the use of an antibody composition as reported herein in a method as reported herein.

In one embodiment the immunoassay is a sandwich immunoassay. In another embodiment the conjugation of the antibody to its conjugation partner is performed by chemically binding via N-terminal and/or ε-amino groups (lysine), ε-amino groups of different lysines, carboxy-, sulfhydryl-, hydroxyl- and/or phenolic functional groups of the amino acid backbone of the antibody and/or sugar alcohol groups of the carbohydrate structure of the antibody. In one embodiment the capture antibody is immobilized via a specific binding pair. In one embodiment the capture antibody is conjugated to biotin and immobilization is performed via immobilized avidin or streptavidin. In one embodiment the tracer antibody is conjugated to the detectable label via a specific binding pair. In one embodiment the tracer antibody is conjugated to digoxygenin and linking to the detectable label is performed via an antibody against digoxygenin. In one embodiment the therapeutic antibody is a human or a humanized antibody. In one embodiment the human or humanized antibody is a monoclonal antibody. In one embodiment the total therapeutic antibody is detected, in another embodiment the active therapeutic antibody is detected, and in a further embodiment the therapeutic antibody is detected which is bound to its antigen.

DETAILED DESCRIPTION OF THE INVENTION

The anti-human IgG antibody denoted M-R10Z8E9 (obtained from the cell line DSM ACC2708) binds to an epitope in the CH2 domain of human immunoglobulin of class G near the glycosylation site Asn297. The herein reported antibody M-1.19.31 (produced by cell line DSM ACC3076) shows a reduced cross-reactivity compared to antibody M-R10Z8E9, binds to a different epitope in the Fab-region as the antibodies M-R10Z8E9 produced by cell line DSM ACC2708, M-1.3.2 produced by cell line DSM ACC3006, M-1.5.8 produced by cell line DSM ACC3007, and M-1.7.10 produced by cell line DSM ACC3008, is not influenced by a neighboring glycosylation site, and can be mixed in an immunoassay for the determining of a therapeutic antibody, especially of Fab therapeutic antibodies, with antibody M-R10Z8E9 produced by cell line DSM ACC2708, antibody M-1.3.2 produced by cell line DSM ACC3006, antibody M-1.5.8 produced by cell line DSM ACC3007, and/or antibody M-1.7.10 produced by cell line DSM ACC3008 as the binding sites of each of the antibodies is present only once in the Fab-fragment of a human or humanized antibody.

The term "therapeutic antibody" denotes an antibody which is tested in clinical studies for approval as human therapeutic and which can be administered to an individual for the treatment of a disease. In one embodiment the therapeutic antibody is a monoclonal antibody. In a further embodiment the therapeutic antibody is obtained from a great ape or an animal transformed with a human antibody locus, or is a human monoclonal antibody, or is a humanized monoclonal antibody. In one embodiment the therapeutic antibody is a human monoclonal antibody. In one embodiment the therapeutic antibody is a humanized monoclonal antibody. Therapeutic antibodies are being used widely for the treatment of various diseases such as oncological diseases (e.g. hematological and solid malignancies including non-Hodgkin's lymphoma, breast cancer, and colorectal cancer), immunological diseases, central nervous diseases, vascular diseases, or infectious diseases. Such antibodies are, for instance, antibodies against CD19, CD20, CD22, HLA-DR, CD33, CD52, EGFR, G250, GD3, HER2, PSMA, CD56, VEGF, VEGF2, CEA, Lewis Y antigen, IL-6 receptor (IL6R), or IGF-1 receptor (IGF1R).

The term "antibody" encompasses the various forms of antibody structures including whole antibodies and antibody fragments. The antibody as reported herein is in one embodiment a human antibody, a humanized antibody, a chimeric antibody, or a T cell antigen depleted antibody. Genetic engineering of antibodies is e.g. described in Morrison, S. L., et al., Proc. Natl. Acad Sci. USA 81 (1984) 6851-6855; U.S. Pat. No. 5,202,238 and U.S. Pat. No. 5,204,244; Riechmann, L., et al., Nature 332 (1988) 323-327; Neuberger, M. S., et al., Nature 314 (1985) 268-270; Lonberg, N., Nat. Biotechnol. 23 (2005) 1117-1125. Depending on the amino acid sequence of the constant region of the heavy chains, antibodies are divided in the classes: IgA, IgD, IgE, IgG, and IgM. Some of these classes are further divided into subclasses (isotypes), i.e. IgG in IgG1, IgG2, IgG3, and IgG4, or IgA in IgA1 and IgA2. According to the immunoglobulin class to which an antibody belongs are the heavy chain constant regions of immunoglobulins are called α (IgA), δ (IgD), ε (IgE), γ (IgG), and μ (IgM), respectively. The term "antibody of human IgG1 class" denotes an antibody in which the amino acid sequence of the constant domains is derived from the amino acid sequence of human IgG1 as denoted in SEQ ID NO: 01, SEQ ID NO: 02, SEQ ID NO: 03, or SEQ ID NO: 04. In such an antibody at least the CH1 domain has to be present. The term includes human antibodies, humanized antibodies, chimeric antibodies and antibody conjugates.

"Humanized" forms of non-human (e.g. rodent) antibodies are chimeric antibodies that contain partial sequences derived from a non-human antibody and from a human antibody. For the most part, humanized antibodies are derived from a human antibody (recipient antibody), in which residues from a hypervariable region are replaced by residues from a hypervariable region of a non-human species (donor antibody), such as mouse, rat, rabbit, or non-human primate, having the desired specificity and affinity. In some instances, framework region (FR) residues of the human antibody are replaced by corresponding non-human residues. Furthermore, humanized antibodies may comprise further modifications, e.g. amino acid residues that are not found in the recipient antibody or in the donor antibody. Such modifications result in variants of such recipient or donor antibody, which are homologous but not identical to the corresponding parent sequence. These modifications are made to further refine antibody performance.

In general, the humanized antibody will comprise substantially all of at least one, and typically two, variable domains, in which all or substantially all of the hypervariable loops correspond to those of a non-human donor antibody and all or substantially all of the FRs are those of a human recipient antibody. The humanized antibody optionally will also comprise at least a portion of an antibody constant region, typically that of a human antibody.

Methods for humanizing non-human antibodies have been described in the art. In one embodiment a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers by substituting hypervariable region sequences for the corresponding sequences of a non-human antibody. Accordingly, such "humanized" antibodies are chimeric antibodies, wherein substantially less than an intact human variable domain has been substituted by the corresponding sequence from a non-human species. In practice, humanized antibodies are typically human antibodies in which some hypervariable region residues and possibly some framework region residues are substituted by residues from analogous sites in rodent or non-human primate antibodies.

The term "monoclonal antibody" as used herein refers to an antibody obtained from a population of substantially homogeneous antibodies, i.e. the individual antibodies comprising the population are identical except for possible naturally occurring mutations that may be present in minor amounts. Monoclonal antibodies are highly specific, being directed against a single antigenic site. Furthermore, in contrast to polyclonal antibody preparations, which include different antibodies directed against different antigenic sites (determinants or epitopes), each monoclonal antibody is directed against a single antigenic site on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies and is not to be construed as requiring production of the antibody by any particular method.

The term "chimeric antibody" denotes an antibody comprising a variable domain, i.e. binding region, from a first species and at least a portion of a constant region derived from a different second source or species, usually prepared by recombinant DNA techniques.

The term "experimental animal" as used herein denotes the members of the families of the order of primates comprising marmosets and tamarins (family Callitrichidae), new world monkeys (family Cebidae), old world monkeys (family Cercopithecidae), dwarf and mouse lemurs (family Cheirogaleidae), aye-aye (family Daubentoniidae), bushbabies and galagos (family Galagonidae), gibbons and lesser apes (family Hylobatidae), indris, sifakas, and relatives (family Indridae), true lemurs (family Lemuridae), lorises (family Loridae), sportive lemurs (family Megaladapidae), tarsiers (family Tarsiidae), as well as crossings thereof.

In one embodiment the experimental animal is selected from the group comprising the members of the families of marmosets and tamarins, old world monkeys, dwarf and mouse lemurs, gibbons and lesser apes, true lemurs, as well as crossings thereof. In this embodiment the closest relatives to mankind, the great apes, especially the group of chimpanzees, bonobos, gorillas and orangutans is excluded. In one embodiment the experimental animal is a member of the genus *Macaca*. In one embodiment the experimental animal is selected from *Macaca fascicularis* (cynomolgus monkey) and *Macaca mulatta* (rhesus-monkey).

A "sample" denotes any tissue or liquid sample obtained from the experimental animal. In one embodiment the sample will be a liquid sample like Saliva, urine, whole blood, plasma or serum. In a further embodiment the sample will be whole blood, plasma or serum.

An "antibody specifically binding to a therapeutic antibody of human IgG1 class and not specifically binding to the antibody of an experimental animal" or an "antibody, which specifically binds to a therapeutic antibody of human IgG1 class and does not specifically bind to the antibody of an experimental animal," binds to a therapeutic antibody of human IgG1 class with a dissociation constant ($=K_{Diss}$) of at least $10^{-8}$ mol/l. Thus, the term "specifically binding" denotes the binding of an antibody or Fab fragment with a dissociation constant ($=K_{Diss}$) of $10^{-8}$ mol/l or less. The terms "not specifically binding" or "does not specifically bind" denote the binding of an antibody or Fab fragment with a dissociation constant ($=K_{Diss}$) of at most $10^{-7}$ mol/l or more, i.e. $10^{-5}$ mol/l. At the same time the property of "not specifically binding to the antibody of the experimental animal" is insured by a $K_{Diss}$ of $10^{-7}$ mol/l or worse. In one embodiment the antibody specifically binding to a therapeutic antibody and not specifically binding to the antibody of an experimental animal will have a $K_{Diss}$-gap of at least 100-fold between its reactivity towards the antibody of human IgG1 class and towards the antibody of the experimental animal.

The binding properties of an antibody, especially the $K_{Diss}$, in one embodiment are assessed by a BIAcore® instrument. In this method binding properties are evaluated by changes in surface plasmon resonance (SPR). It is convenient to bind the antibody under investigation to the solid phase (called chip) and to assess binding of a monoclonal antibody, a polyclonal antibody or even of serum comprising IgG to this coated chip.

The term "epitope" denotes a protein determinant capable of specifically binding to an antibody. Epitopes usually consist of chemically active surface groupings of molecules such as amino acids or sugar side chains and usually epitopes have specific three dimensional structural characteristics, as well as specific charge characteristics. Conformational and non-conformational epitopes are distinguished in that the binding to the former but not the latter is lost in the presence of denaturing solvents. In one embodiment an antibody as reported herein binds to native but not to denatured human IgG1.

The term "binding to the same epitope as an antibody produced by the cell line DSM ACC3076" as used herein refers to an antibody that binds to the same epitope on human IgG1 to which the antibody M-1.19.31 (produced by cell line DSM ACC3076) binds. The epitope binding property of an antibody binding to an antibody of human IgG1 class as reported herein may be determined using techniques known in the art. The binding to human IgG1 can be determined by Surface Plasmon Resonance (SPR) at 25° C. in an in vitro competitive binding inhibition assay to determine the ability of the test antibody to inhibit binding of antibody M-1.19.31 to human IgG1. This can be investigated by a BIAcore assay (Pharmacia Biosensor AB, Uppsala, Sweden) as reported e.g. in Example 12. In Example 12 the percentage (%) of expected binding response of the antibody binding to an antibody of human IgG1 class as reported herein competing with the bound antibody M-1.19.31 is calculated by Formula I $$100 * \frac{\text{relative Response (general\_stability\_early)}}{r_{Max}}, \quad \text{(Formula I)}$$

where $r_{Max}$ is calculated by Formula II $$\frac{\text{relative Response (general\_stability\_late)} * }{\frac{\text{antibody molecular weight}}{\text{antigen molecular weight}}}, \quad \text{(Formula II)}$$

as described in BIAcore assay epitope mapping instructions. A minimal binding response is also calculated from the pairs of identical antibody 1 and 2 (see Example 12). Thereof the obtained maximal value+50% is set as threshold for significant competition and, thus, significant binding to the same epitope.

In one aspect as reported herein are antibodies that compete with antibody M-1.19.31 for binding to an antibody of human IgG1 class. Such binding competition may be determined using techniques known in the art. The binding of the antibody is determined at 25° C. by Surface Plasmon Resonance (SPR) in an in vitro competitive binding inhibition assay to determine the ability of the test antibody to inhibit binding of antibody M-1.19.31 to an antibody of human IgG1 class. This can be investigated by a BIAcore assay (Pharmacia Biosensor AB, Uppsala, Sweden) as e.g. in Example 12.

The antibody specifically binding to a (therapeutic) antibody of human IgG1 class and not specifically binding to the antibody of the experimental animal is in one embodiment a monoclonal antibody, or a fragment of such an antibody, or a genetic construct comprising the binding domain of such an antibody. Any antibody fragment retaining the above criteria of specifically binding to the antibody of human IgG1 class and of not specifically binding to the antibody of an experimental animal can be used.

Various aspects connected to the application of a therapeutic antibody of human IgG1 class in an experimental animal may have to be assessed during pre-clinical studies. In certain settings it may be relevant to analyze the total amount of therapeutic antibody of human IgG1 class present, or it may be important to analyze certain fragments of a therapeutic antibody of human IgG1 class, or certain modifications of a therapeutic antibody of human IgG1 class, or the concentration of therapeutic antibody of human IgG1 class bound to an antigen, or the fraction of a therapeutic antibody of human IgG1 class still capable of specifically binding to an antigen. In one embodiment the antibodies and methods as reported herein can be used to detect the total, active, ADA-bound, or antigen-bound therapeutic antibody of human IgG1 class, respectively. The term "total therapeutic antibody" denotes any antibody detected irrespective of whether the antibody is active (i.e. still reactive with its antigen), inactive, and/or antigen-bound.

The total therapeutic antibody can be divided in active therapeutic antibody and inactive therapeutic antibody.

The term "active therapeutic antibody" denotes the therapeutic antibody present in an experimental animal that still is capable of binding its antigen. Such antibodies, e.g., have not bound its antigen or any other molecule at its antigen binding site.

The "inactive therapeutic antibody" can be divided in antigen-bound therapeutic antibody, anti-therapeutic-antibody antibody-bound therapeutic antibody (anti-drug antibody-bound therapeutic antibody; ADA-bound therapeutic antibody), and denatured antibody.

The term "antigen-bound therapeutic antibody" denotes the therapeutic antibody as present in the circulation of an experimental animal that is bound to its antigen.

Total, active, ADA-bound, or antigen-bound therapeutic antibody as defined above can be directly detected with the antibody and in methods as reported herein. Additionally it is possible to detect other forms of non-active therapeutic antibodies, such as therapeutic antibodies bound by anti-drug antibodies, or anti-idiotype antibodies, or especially neutralizing anti-drug antibodies.

In addition, it is also possible to indirectly assess any "inactive therapeutic antibody". Such inactive therapeutic antibody may, e.g., be a therapeutic antibody bound to its antigen, or the therapeutic antibody bound to a cross-reactive antigen, or the therapeutic antibody blocked by an auto- or anti-idiotypic antibody against the therapeutic antibody. In case the total antibody amounts to more than the sum of active antibody and antigen-bound antibody, an additional fraction of antibody comprising the inactive antibody not bound to its corresponding antigen will be present.

Total therapeutic antibody for example can be detected in a so-called competitive immunoassay system or in a so-called sandwich type assay system. Such assay may be performed in one embodiment without washing steps (homogeneous immunoassay), or as in another embodiment with washing steps (heterogeneous immunoassay).

In one embodiment the total therapeutic antibody is detected in a sandwich type immunoassay, wherein an antibody which is specifically binding to a therapeutic antibody and not specifically binding to the antibody of the experimental animal is used at both sides of the sandwich. The antibody used at one side of such sandwich is bound or capable of binding to a solid phase (often referred to as capture antibody), whereas the antibody at the other side of such sandwich is labeled in such a manner that direct or indirect detection is facilitated (so-called detection antibody). The amount of detection antibody bound in such sandwich assay procedure is directly correlated to the amount of therapeutic antibody in the sample investigated.

Detection of active therapeutic antibody in a sample may be achieved by convenient state of the art procedures. However, the detection of total therapeutic antibody or of the fraction of therapeutic antibody bound to its antigen is rather complicated and requires quite different assay set-ups and especially requires tailor-made reagents for each of the different assays. With the antibody as reported herein that is specifically binding to a therapeutic antibody and not specifically binding to the antibody of the experimental animal it is possible to assess the fraction of active therapeutic antibody, total therapeutic antibody, ADA-bound, or antigen-bound therapeutic antibody in test systems which are analogues to each other. This kind of comparative assessment of total, active, ADA-bound, or antigen-bound therapeutic has benefits once quantitative comparisons are made in between these various fractions of therapeutic antibody.

In one embodiment a sandwich type assay format is set up to detect the active therapeutic antibody. In one embodiment the antibody which is specifically binding to a therapeutic antibody and not specifically binding to the antibody of the experimental animal is used as capture antibody and the detection side of such sandwich assay either makes use of the antigen in a labeled form or after binding of the antigen makes use of a second antibody not binding to or competing with the epitope recognized by the therapeutic antibody, wherein the second antibody is specifically detectable and/or is labeled in such a manner that direct or indirect detection is facilitated.

The antigen-bound therapeutic antibody is in one embodiment detected in a sandwich type assay format using the antibody specifically binding to a therapeutic antibody and not specifically binding to the antibody of the experimental animal as a capture reagent. In the detection as in one embodiment a second antibody is used which is binding to the antigen at an epitope which does not compete with the epitope of the therapeutic antibody. The second antibody in one embodiment is labeled in such a manner that direct or indirect detection is facilitated.

For direct detection the labeling group can be selected from any known detectable marker groups, such as dyes, luminescent labeling groups such as chemoluminescent groups, e.g. acridinium esters or dioxetanes, or fluorescent dyes, e.g. fluorescein, coumarin, rhodamine, oxazine, resorufin, cyanine and derivatives thereof. Other examples of labeling groups are luminescent metal complexes, such as ruthenium or europium complexes, enzymes, e.g. as used for ELISA or for CEDIA (Cloned Enzyme Donor Immunoassay), and radioisotopes. Metal chelates which can be detected by electrochemoluminescence are also in one embodiment signal-emitting groups used as detectable labels, with particular preference being given to ruthenium chelates. In one embodiment the labeling group is a ruthenium (bispyridyl)$_3^{2+}$ chelate.

Indirect detection systems comprise, for example, that the detection reagent, e.g. the detection antibody, is labeled with a first partner of a binding pair. Examples of suitable binding pairs are hapten or antigen/antibody, biotin or biotin analogues such as aminobiotin, iminobiotin or desthiobiotin/avidin or streptavidin, sugar/lectin, nucleic acid or nucleic acid analogue/complementary nucleic acid, and receptor/ligand, e.g., steroid hormone receptor/steroid hormone. In one embodiment the first binding pair member is selected from hapten, antigen and hormone. In one embodiment the hapten is selected from digoxin and biotin and analogues thereof. The second partner of such binding pair, e.g. an antibody, streptavidin, etc., usually is labeled to allow for direct detection, e.g., by the labels as mentioned above.

In all the above immunological detection methods reagent conditions are chosen which allow for binding of the reagents employed, e.g. for binding of an antibody to its corresponding antigen. The skilled artisan refers to the result of such binding event by using the term complex. The complex formed in a method as reported herein is correlated by state of the art procedures to the corresponding concentration of the therapeutic antibody. Depending on the detection reagent employed this correlating step will result in the concentration of total, active, ADA-bound, or antigen-bound therapeutic antibody.

As the skilled artisan will appreciate that the methods as reported herein will reveal the concentrations of total, antigen-bound, active or even inactive therapeutic antibody. Due to the use of one and the same reagent, i.e. the antibody specifically binding to a therapeutic antibody and not specifically binding to the antibody of the experimental animal, in the different assays the values obtained can be easily compared to each other and even ratios thereof can be assessed. In a further embodiment the method relates to the ratio of active to total therapeutic antibody. This ratio may well serve as an indicator for the efficacy of a therapeutic antibody.

It has been found that there is one epitope that is present on antibodies of human IgG1 class and that is not present of antibodies of other human IgG classes, such as IgG2, IgG3 and IgG4, and which is also not present on the antibody of an experimental animal, especially on the immunoglobulins of a cynomolgus monkey or rhesus-monkey. This epitope is characterized by its binding to the antibody M-1.19.31 produced by the deposited cell line DSM ACC3076. Therefore one aspect as reported herein is an antibody produced by the cell line DSM ACC3076.

As the epitope recognized by the antibody produced by the deposited cell line is unique in the Fab region of an antibody of human IgG1 class, another aspect as reported herein is the epitope binding to the antibody obtained from the deposited cell line DSM ACC3076. As the antibody has been identified by its binding to an antibody Fab fragment the epitope is further characterized in being on the Fab fragment of an antibody of human IgG1 class. In one embodiment the epitope is characterized in being on the CH1 domain of human IgG1. In one aspect as reported herein the antibody is specifically binding to a therapeutic antibody of human IgG1 class and not specifically binding to the antibody of an experimental animal and is characterized in that the antibody is an antibody binding to the same epitope as the antibody produced by the cell line DSM ACC3076.

For example, a method can be used in which epitope identity or overlap of an epitope binding to two different antibodies is determined with the help of a competitive test system. For this purpose, for example with the help of an enzyme immunoassay, there is tested the extent to which the antibody in question competes with the known antibody for the binding to an immobilized target antigen. For this purpose, an appropriately immobilized target antigen is incubated with the known antibody in labeled form and an excess of the antibody in question. By detection of the bound labeling there can easily be ascertained the extent to which the antibody in question can displace the known antibody from the binding. If there is a displacement of more than 20%, in another embodiment of more than 30%, at the same concentration or a displacement of more than 70%, in another embodiment of more than 80%, at higher concentrations, in one embodiment in the case of $10^3$-$10^5$-fold excess of the antibody in question, referred to the known antibody, then epitope overlap is present and both antibodies bind to the same or an overlapping epitope.

The specificity of the antibody obtained from the deposited cell lines DSM ACC3076 can be shown in a sandwich-ELISA employing each a biotinylated and a digoxygenylated variant of the respective antibodies and serum from different species. In the assay (see FIG. 1 for scheme) capture and detection antibodies are obtained from the same cell line binding to identical epitopes. To be a generally applicable assay for the detection and quantification of human IgG in the serum of an experimental animal, such an assay requires an anti-human IgG antibody whose binding site is independent from any secondary antibody modification, such as e.g. glycosylation sites or potential deamidation sites. Otherwise it would be necessary to optimize the assay for each new therapeutic antibody to be detected and quantified. Furthermore the herein reported antibody is also different to the analyzed therapeutic antibody and can be employed as reference standard and positive control.

It can be seen that the antibody as reported herein is highly specific for human and chimpanzee immunoglobulin of the immunoglobulin class G and shows a better interspecies specificity than the antibody M-R10Z8E9 and does not specifically bind to the immunoglobulin of class G of an experimental animal.

The specificity of the antibody as reported herein can also be shown in a surface plasmon resonance experiment using the BIAcore technology. By using dot-blot experiments it can be shown that the epitope bound by the antibody as reported herein is a conformational epitope as binding is lost to denatured human immunoglobulin (FIGS. 2A and 2B).

Another aspect as reported herein is an assay for quantifying a human antibody of human IgG1 class or a derivative thereof, such as a Fab-fragment comprising a human IgG1 CH1 domain, in a sample obtained from an experimental animal comprising a biotinylated antibody as reported herein as capture antibody and a digoxygenylated antibody as reported herein as tracer antibody. In FIG. 3 the schematic assay set-up is shown (capture antibody e.g. biotinylated M-1.19.31, analyte: Fab-fragment of human antibody, tracer antibody e.g. digoxigenylated M-1.3.2). This assay requires capture and tracer antibodies which bind to the Fab fragment of human IgG on two different epitopes.

Another aspect as reported herein is an assay comprising a capture and tracer antibody binding specifically to epitopes on different domains of a human IgG. In this assay only an intact therapeutic antibody will result in a positive assay result and a detectable signal. In one embodiment the capture antibody and the tracer antibody are independently selected from the antibodies M-1.3.2, M-1.5.8, M-1.7.10 and M-1.19.31 on the one hand and the antibody M-R10Z8E9 on the other hand. In an exemplary assay according to this aspect to proof structural integrity of a human IgG in an experimental animal as capture antibody biotinylated M-R10Z8E9, as analyte an anti-IL13Rα1 antibody, and as tracer antibody digoxigenylated M-1.19.31 can be employed (in FIGS. 4A and 4B the schematic assay set-up and a calibration curve for this assay is shown, respectively).

A further aspect as reported herein is an assay in which the anti-human IgG antibody is used as a reference standard and/or positive control to mimic an anti-drug antibody (ADA). This can be useful during assay development to determine optimal assay conditions and test robustness of the assay, i.e. to check assay performance with different standard reagents/positive controls. Especially advantageous is this set-up in view of the fact that an ADA will be polyclonal and probably be directed against both, the Fab fragment and the Fc part.

In a further aspect as reported herein the antibody obtained from the cell line DSM ACC3076 is used as the antibody specifically binding to a therapeutic antibody of human IgG1 class and not specifically binding to the antibody of the experimental animal in a method as reported herein.

One aspect as reported herein relates to the use of an antibody which is specifically binding to a therapeutic antibody of human IgG1 class and not specifically binding to the antibody of an experimental animal for determining the concentration of total, active, ADA-bound, or antigen-bound therapeutic antibody of human IgG1 class in a sample obtained from an experimental animal. In one embodiment the antibody used in the method is selected from an antibody binding to the same or an overlapping epitope as recognized by the antibody obtained from the cell line DSM ACC3076.

One aspect as reported herein relates to the use of two antibodies which both are specifically binding to a therapeutic antibody of human IgG1 class and not specifically binding to the antibody of an experimental animal for determining the concentration of total, active, ADA-bound, or antigen-bound therapeutic antibody of human IgG1 class in a sample obtained from an experimental animal, wherein one of the antibodies is the capture antibody and one of the antibodies is the tracer antibody. In one embodiment the therapeutic antibody is a Fab fragment.

The hybridoma cell lines MAB<h-Fc gamma>M-R10Z8E9 (Deposition No. DSM ACC2708), MAK<H-IgG>M-1.3.2 (Deposition No. DSM ACC3006), MAK<H-IgG>M-1.5.8 (Deposition No. DSM ACC3007), MAK<H-

IgG>M-1.7.10 (Deposition No. DSM ACC3008), MAK<H-IgG>M-1.19.31 (Deposition No. DSM AC3076), expressing antibodies M-1.3.2, M-1.5.8, M-1.7.10, and M-1.19.31, respectively, were deposited, under the Budapest Treaty on and meet the conditions of the international recognition of the deposit of microorganisms for the purposes of patent procedure, with Deutsche Sammlung von Mikroorganismen and Zellkulturen GmbH (DSMZ), Inhoffenstr. 7B, D-38124 Braunschweig, Germany.

| Cell line | Deposition No. | Date of Deposit |
|---|---|---|
| MAB<h-Fc gamma>M-R10Z8E9 | DSM ACC2708 | 22 Dec. 2004 |
| MAK<H-IgG>M-1.3.2 | DSM ACC3006 | 24 Sep. 2009 |
| MAK<H-IgG>M-1.5.8 | DSM ACC3007 | 24 Sep. 2009 |
| MAK<H-IgG>M-1.7.10 | DSM ACC3008 | 24 Sep. 2009 |
| MAK<H-IgG>M- 1.19.31 | DSM ACC3076 | 30 Jun. 2010 |

The cell lines and antibodies obtainable from the cell lines are aspects of the current invention.

SPECIFIC EMBODIMENTS

Embodiment 1

A monoclonal antibody characterized in that the antibody specifically binds to an antibody of human IgG1 class and does not specifically bind to the immunoglobulin of rhesus-monkey, marmoset monkey, baboon monkey and cynomolgus monkey.

Embodiment 2

The antibody according to Embodiment 1, characterized in that the antibody binds to an antibody of human IgG1 class with a kappa light chain.

Embodiment 3

The antibody according to any one of the preceding Embodiments, characterized in that the antibody does not bind to an antibody of human IgG1 class with a lambda light chain.

Embodiment 4

The antibody according to any one of Embodiments 1 and 2, characterized in that the antibody binds to an antibody of human IgG1 class with a lambda light chain.

Embodiment 5

The antibody according to any one of Embodiments 1, 2 and 4, characterized in that the antibody does not bind to an antibody of human IgG2 class.

Embodiment 6

The antibody according to any one of Embodiments 1, 2 and 4 to 5, characterized in that the antibody does not bind to an antibody of human IgG4 class.

Embodiment 7

The antibody according to any one of Embodiments 1, 2 and 4 to 6, characterized in that the antibody binds to the Fab of an antibody of human IgG1 class with a lambda light chain.

Embodiment 8

The antibody according to any one of the preceding Embodiments, characterized in that the antibody binds to the Fab of an antibody of human IgG1 class with a kappa light chain.

Embodiment 9

The antibody according to any one of the preceding Embodiments, characterized in the antibody does not bind to an antibody of human IgG3 class.

Embodiment 10

The antibody according to any one of the preceding Embodiments, characterized in that the antibody is a non-human animal derived antibody.

Embodiment 11

The antibody according to any one of the preceding Embodiments, characterized in that the antibody is specifically binding to the heavy chain constant region 1 of an antibody of human IgG1 class.

Embodiment 12

The monoclonal antibody obtained from the cell line DSM ACC3006.

Embodiment 13

A monoclonal antibody characterized in that the antibody is specifically binding to the same or an overlapping epitope as the antibody produced by the cell line DSM ACC3006, or the cell line DSM ACC3007

Embodiment 14

The cell line DSM ACC3006.

Embodiment 15

The monoclonal antibody obtained from the cell line DSM ACC3007.

Embodiment 16

The monoclonal antibody obtained from the cell line DSM ACC3008.

Embodiment 17

A monoclonal antibody characterized in that the antibody is specifically binding to the same or an overlapping epitope as the antibody produced by the cell line DSM ACC3008.

Embodiment 18

The cell line DSM ACC3007.

Embodiment 19

The cell line DSM ACC3008.

Embodiment 20

The monoclonal antibody obtained from the cell line DSM ACC3076.

Embodiment 21

A monoclonal antibody characterized in that the antibody is specifically binding to the same or an overlapping epitope as the antibody produced by the cell line DSM ACC3076.

Embodiment 22

The cell line DSM ACC3076.

Embodiment 23

The use of an antibody according to any one of Embodiments 1 to 13 and 15 to 17 and 20 to 21 in an immunoassay.

Embodiment 24

Kit comprising
a) an antibody obtained from cell line DSM ACC3006, or DSM ACC3007, or DSM ACC3008, or DSM ACC3076 as capture reagent,
b) an antibody obtained from cell line DSM ACC3006, or DSM ACC3007, or DSM ACC3008, or DSM ACC3076 as detection reagent.

Embodiment 25

A method for detecting a therapeutic antibody of human IgG1 class in a sample obtained from an experimental animal comprising the steps of
a) incubating a sample to be analyzed with a monoclonal antibody according to any one of Embodiments 1 to 13 and 15 to 17 and 20 to 21,
b) optionally incubating the sample with a reagent for the selective detection of total, active, ADA-bound, or antigen-bound therapeutic antibody, and
c) correlating the complex formed in (a) or (b) to the presence of the therapeutic antibody and thereby detecting the therapeutic antibody.

Embodiment 26

A Method for determining a therapeutic antibody of human IgG1 class in a sample obtained from an experimental animal using an immunoassay comprising a capture antibody and a tracer antibody, characterized in that the capture antibody and/or the tracer antibody are both independently selected from an antibody according to any one of Embodiments 1 to 13 and 15 to 17 and 20 to 21.

Embodiment 27

The method according to any one of Embodiments 25 to 26, characterized in that the therapeutic antibody is a Fab.

Embodiment 28

The antibody according to Embodiments 1 to 13 and 15 to 17 and 20 to 21 and the method according to any one of Embodiments 25 to 27, characterized in that the experimental animal is selected from the group comprising the members of the families of marmosets and tamarins, old world monkeys, dwarf and mouse lemurs, gibbons and lesser apes, true lemurs, as well as crossings thereof.

Embodiment 29

The use of an antibody which is specifically binding to a therapeutic antibody of human IgG1 class and not specifically binding to the immunoglobulin of an experimental animal for determining the concentration of total, active, ADA-bound, or antigen-bound therapeutic antibody in a sample obtained from an experimental animal whereby the antibody is an antibody according to any one of Embodiments 1 to 13 and 15 to 17 and 20 to 21.

Embodiment 30

An antibody composition, characterized in comprising a mixture of the antibodies produced by the cell line DSM ACC3006, and/or the cell line DSM ACC3007, and/or the cell line DSM ACC3008, and/or the cell line DSM ACC3076, and/or the cell line DSM ACC2708.

Embodiment 31

The use of an antibody composition according to Embodiment 30 in a method according to any one of Embodiments 25 to 27.

The following examples and figures are provided to aid the understanding of the present invention, the true scope of which is set forth in the appended claims. It is understood that modifications can be made in the procedures set forth without departing from the spirit of the invention.

DESCRIPTION OF THE FIGURES

SEQ ID NO: 01 Human IgG1 (Caucasian Allotype)
SEQ ID NO: 02 Human IgG1 (Afroamerican Allotype)
SEQ ID NO: 03 Human IgG1 variant (Caucasian Allotype)
SEQ ID NO: 04 Human IgG1 CH1 domain

DESCRIPTION OF THE FIGURES

Figure 1:
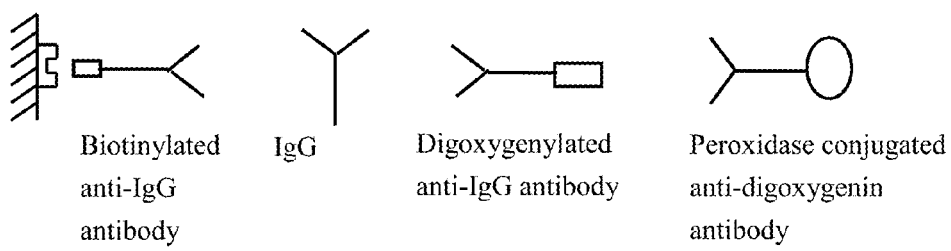

FIG. 1 Assay format of fully generic Assay for quantification of human antibodies (human IgG) in an experimental animal.

Figure 2:
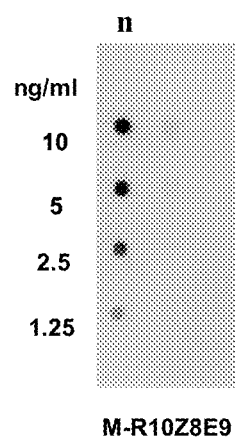
Figure 2:
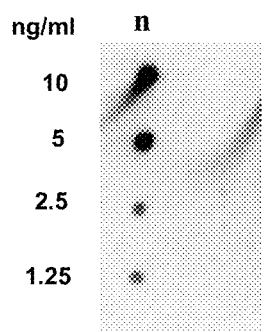

FIGS. 2A and 2B Dot Blot of anti-human IgG antibodies; as exemplary reference antibody an antibody against P-selectin has been chosen; the reference antibody is dotted is native (left column) and denatured (right column) form onto a nitrocellulose membrane and detected by the respective digoxigenylated anti-human IgG antibodies; 2A) M-R10Z8E9, 2B) M-1.19.31.

Figure 3:
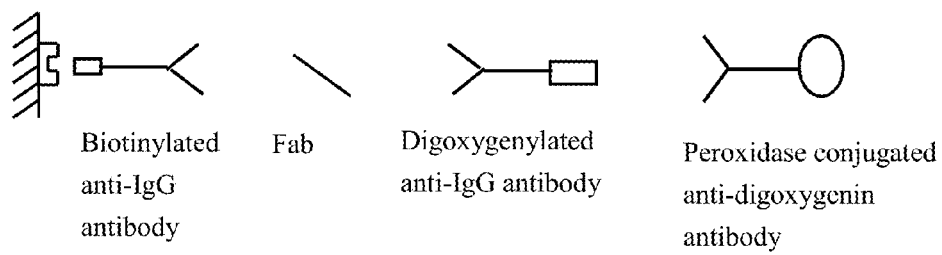

FIG. 3 Assay for quantifying human antibody derivates in a sample obtained from an experimental animal: schematic assay set-up.

Figure 4:
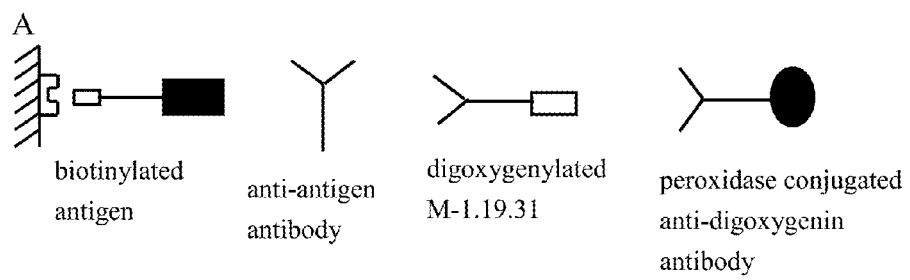
Figure 4:
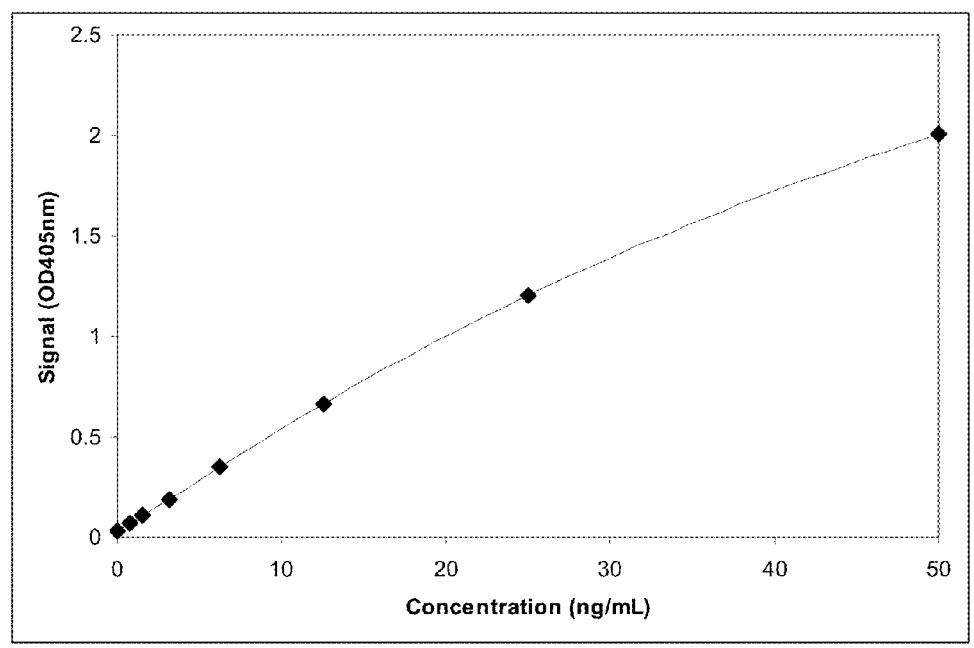

FIGS. 4A and 4B Assay to proof structural integrity of human IgG in an experimental animal: 4A) schematic assay set-up, 4B) calibration curve.

EXAMPLE 1

Preparation of the F(Ab')$_2$ Fragment of Human IgG (Immunogen)

The full length human antibody of the class G (human IgG) in 100 mM sodium citrate buffer, pH 3.7 was incubated with pepsin (1 μg pepsin per mg IgG). The fragmentation was analyzed by analytical gel filtration and stopped after 90 minutes by adjusting the pH value to 6.5 by the addition of potassium phosphate. After dialysis of the mixture against 10 mM sodium citrate buffer with 10 mM sodium chloride, pH 5.5, the solution was applied to an SP-sepharose chromatography column and the isolated fractions eluted in a salt gradient were analyzed individually by analytical gel filtration. The pool containing the antibody F(ab')$_2$ fragments were applied to an affinity matrix with immobilized polyclonal antibodies against human Fcγ to eliminate trace amounts of Fcγ fragments. The flow through was pooled, concentrated to about 16 mg/ml and finally applied to a gel filtration column (Superdex 200).

EXAMPLE 2

Generation of Monoclonal Anti-Human IgG Antibodies a) Immunization of Mice

Female NMRI mice, 8-12 weeks of age, were each primarily immunized intraperitoneally with 100 μg of the antibody F(ab')$_2$ fragments prepared according to Example 1 mixed with CFA (Complete Freund's Adjuvant). Two further intraperitoneal immunization steps followed after 6 and 10 weeks, each with 100 μg of the antibody F(ab')$_2$ fragments per mouse mixed with IFA (Incomplete Freund's adjuvant). Subsequently, intravenous boost immunizations were done, each with 50 μg of antibody F(ab')$_2$ fragments in PBS (phosphate buffered saline) three days before the fusion.
b) Fusion and Cloning Spleen cells of the mice immunized according to a) were fused with myeloma cells according to Galfré and Milstein (Galfré, G. and Milstein, C, Methods Enzymol. 73 (1981) 3-46). Approximately $2.1 \times 10^8$ splenocytes were mixed with $4.2 \times 10^7$ myeloma cells (P3x63-Ag8.653, ATCC CRL1580) and centrifuged (10 min. at 300×g and 4° C.). The cells were washed afterwards once with the culture medium RPMI 1640 without FCS (fetal calf serum), and centrifuged again at 400×g in a 50 ml pointed vial. Thereafter, 1 ml of PEG (poly (ethylene glycol), molecular weight 4,000 g/mol) was added, mixing was done by the pipetting. After 1 min. in a water bath at 37° C., 5 ml of RPMI 1640 without FCS were added drop wise, the suspension was mixed, RPMI 1640 with 10% (v/v) FCS was added to a final volume of 50 ml, and then centrifuged. The sedimented cells were resuspended in RPMI 1640 with 10% FCS, and plated in hypoxanthine-azaserine selection medium (100 mmol/l hypoxanthine, 1 μg/ml azaserine in RPMI 1640 with 10% FCS) containing the growth factor recombinant murine interleukin 6 (Peprotech, 0.5 ng/ml). After 11 days, the primary cultures were assayed for specific antibody synthesis (see Example 3). Primary cultures exhibiting binding to biotinylated antibody F(ab')$_2$ fragments as well as to biotinylated human normal IgG were individualized by single cell deposition into 96-well cell culture plates using a flow cytometer (FACSAria, BD Biosciences) in medium containing the growth factor recombinant murine interleukin 6 (Peprotech, 0.5 ng/ml). By following this protocol, the cell line DSM ACC3076 was obtained.
c) Production of Immunoglobulin The hybridoma cell line obtained in b) was inoculated at an initial cell density (live cells) of about $2 \times 10^5$ cells per ml in RPMI 1640 supplemented with 10% FCS, and commonly used supplements and expanded in a T-flask (Celline, IBS) for a period of approximately three weeks. Purification of the antibodies from the culture supernatants was done according to standard protein chemical methods, e.g. as those reported in Bruck, C., et al., Methods Enzymol. 121 (1986) 587-596.

EXAMPLE 3

Screening Assays for Detection of Anti-Human IgG Antibodies a) Primary Screening for Antibodies Binding to Human IgG For the determination of the specificity of the antibodies in the culture supernatant of the hybridoma cell, MTPs (microtiter plates) pre-coated with recombinant streptavidin (MicroCoat, Bernried, lot MC 1098) were coated with biotinylated humanized IgG used for the immunization process, 250 ng/ml, or biotinylated human IgG, 250 ng/ml, respectively, in PBS supplemented with 1.0% (w/v) BSA II (100 μl per well, 60 min. incubation at ambient temperature, with shaking), and subsequently washed three times with 0.9% (w/v) NaCl/0.05% Tween® 20. In the next step, per well 100 μl of the antibody solution to be assayed (culture supernatant) were added, and incubated for 60 min. at ambient temperature, with shaking. After three wash steps with 0.9% (w/v) NaCl/0.05% Tween® 20 per well, 100 μl of a horseradish peroxidase-labeled F(ab')$_2$ fragment of a polyclonal sheep anti-mouse Fcγ antibody were added for the detection of bound sample antibody, and incubated for 60 min. at ambient temperature, with shaking Subsequently, washing was performed as above. Finally, per well 100 μl of ABTS® (Roche Diagnostics GmbH, Mannheim, Germany; catalog no. 1684302) were added. After 30 min. incubation at ambient temperature, the extinction (OD) was measured at 405 and 492 nm [405/492] in a commercial microtiter plate ELISA Reader. This screening led to a selection of antibodies binding well to humanized IgG as well as to human IgG. This selection of antibodies was further subjected to assay b).
b) Selection of Antibodies with Minimal Cross-Reactivity to IgG of Other Species Biotinylated human IgG was bound to the wells of a streptavidin-coated microtiterplate (SA-MTP) in the first step. The excess of unbound antibody was removed by washing. Afterwards the samples and the reference standards (e.g. anti-human IgG antibody as obtained with Example 2) were diluted in buffer and 10% cynomolgus serum. Diluted samples were added to the plate and incubated for 60 min. at ambient temperature, with shaking. After having washed away unbound substances, the human IgG of the first step in digoxygenylated form was added to the wells of the plate and incubated for another 60 min. After washing, the bound digoxygenylated antibody was detected with an anti-digoxygenin antibody-HRP conjugate. The HRP (horseradish peroxidase) of the antibody-enzyme conjugates catalyzes the color reaction of ABTS substrate. The signal is measured by ELISA reader at 405 nm wavelength (reference wavelength: 490 nm). Absorbance values of each serum sample were determined in triplicates.

Antibodies with high assay response in cynomolgus serum as well as in buffer were selected. This second screening led to a selection of antibodies binding well to human IgG with minimal cross-reactivity to IgG of other species.

EXAMPLE 4

Assessment of Antibody Binding/Specificity by Surface Plasmon Resonance

All measurements were performed with the BIAcore® T100 instrument using a CM5-chip. Coating of this chip with an antibody was achieved by standard amine coupling. Unless otherwise indicated, all incubations were performed in HBS-buffer (HEPES, NaCl, pH 7.4) at 25° C. A saturating amount of a polyclonal goat anti-mouse Fc-gamma antibody was immobilized by amine coupling on one flow cell of the CM5-chip. Subsequently, the monoclonal mouse antibody directed against human IgG was injected for 60 seconds at a flow rate of 30 µl/min and was bound by the anti mouse Fc antibody. All animal sera were diluted in HBS buffer. Binding was analyzed by injection of the 1 in 100 diluted sera and incubation for 60 sec. at a flow rate of 30 µl/min. Dissociation was measured by washing the chip surface with HBS buffer for 180 sec. Using BIAevaluation Software from BIAcore® the dissociation constant values ($=K_D$) were calculated with a 1:1 Langmuir fitting model. For all animal sera this calculation was based on the assumption that the IgG level is 15 mg/ml. The signal values 80 sec. after start of the injection of the test antibody were chosen for the comparison of the amount of IgG bound (see Table 1).

TABLE 1

Binding signals [RU] and $K_D$-values for binding of animal sera to different monoclonal anti-human IgG antibodies.

| | Antibody | | | |
|---|---|---|---|---|
| | M-R10Z8E9 | | M-1.19.31 | |
| Sample (serum) | Bound RU | $K_D$ mol/l | Bound RU | $K_D$ mol/l |
| Chimpanzee | 159 | $2.21 \times 10^{-10}$ | 352 | $4.92 \times 10^{-9}$ |
| Human | 151.3 | $1.77 \times 10^{-10}$ | 356 | $1.52 \times 10^{-8}$ |
| Dog | 35.5 | $3.17 \times 10^{-8}$ | 3 | no binding |
| Rhesus-monkey | −1.9 | no binding | 36 | $2.15 \times 10^{-6}$ |
| Marmoset | 18.9 | $2.04 \times 10^{-7}$ | 0 | no binding |
| Baboon | −1.5 | no binding | 41 | $4.53 \times 10^{-6}$ |
| Cynomolgus | −1.4 | no binding | 31 | $1.23 \times 10^{-6}$ |

EXAMPLE 5 a) Purification of Mouse Monoclonal Anti-Human IgG Antibody

The fermentation supernatant of the cell line obtained in Example 2 was concentrated about tenfold and transferred to a buffer with 20 mM TRIS, 1 M ammonium sulfate, pH 9.0, and applied to a protein A-sepharose chromatography column. The eluate obtained with 0.2 M sodium citrate, 0.2 M ammonium sulfate at pH 5.0 was dialyzed against phosphate buffer, pH 7.5. Contaminants of bovine IgG (from FCS in the fermentation broth) were separated by immunoadsorption with immobilized antibodies against bovine IgG.

b) Preparation of Biotinylated Anti-Human IgG Antibody

The anti-human IgG antibody obtained in a) in phosphate buffer, pH 8.5, was adjusted to a protein concentration of about 5 mg/ml. D-biotinoyl-aminocaproic acid-N-hydroxysuccinimide was dissolved in DMSO and added to the antibody solution in a molar ratio of 1:5. The reaction was stopped after 60 min. by adding L-lysine, and the surplus of the labeling reagent was removed by dialysis against 50 mM potassium phosphate buffer, with 150 mM NaCl, pH 7.5.

c) Preparation of Digoxigenylated Anti-Human IgG Antibody

The anti-human IgG antibody obtained in a) in phosphate buffer, pH 8.5, was adjusted to a protein concentration of about 5 mg/ml. Digoxigenin 3-O-methylcarbonyl-ε-aminocaproic acid-N-hydroxysuccinimide was dissolved in DMSO and added to the antibody solution in a molar ratio of 1:4. The reaction was stopped after 60 min. by adding L-lysine, and the surplus of the labeling reagent was removed by dialysis against 50 mM potassium phosphate buffer, with 150 mM NaCl, pH 7.5.

EXAMPLE 6

Fully Generic Assay for Quantification of Human Antibodies (Human IgG) in a Sample from an Experimental Animal Biotinylated antibody M-1.19.31 can be bound to a streptavidin-coated microtiter plate (SA-MTP) in the first step. The excess of unbound antibody can be removed by washing. Samples/standards, e.g. anti-IL1R antibody, anti-IL13Rα1 antibody, anti-Abeta antibody and anti-IL6R antibody, spiked in cynomolgus serum can be added in a concentration series to the plate and incubated for 60 min. at ambient temperature, with shaking. After having washed away unbound antibodies, 100 µl digoxygenylated antibody M-1.19.31 can be added to the plate. After washing, the bound digoxygenylated antibodies can be detected with an anti-digoxygenin-antibody-HRP conjugate. Absorbance values of each serum sample were determined in triplicates (see FIG. 1 for schematic method).

EXAMPLE 7

Assay for Quantification of Human Antibody Derivates (e.g. Fab-Fragments) in a Sample from an Experimental Animal Biotinylated antibody M-1.19.31 can be bound to streptavidin-coated microtiter plates (SA-MTP) in the first step. The excess of unbound antibody can be removed by washing. Samples/standards, e.g. anti-IGF1R antibody Fab fragment, spiked in cynomolgus serum can be added to the wells and incubated for 60 min. at ambient temperature, with shaking. After having washed away unbound antibodies, 100 µl digoxigenylated antibody M-1.3.2 can be added to each well of the plate. After washing, the bound digoxygenylated antibodies can be detected with an anti-digoxygenin antibody-HRP conjugate. Absorbance values of each serum sample can be determined in triplicates (see FIG. 3 for schematic method).

EXAMPLE 8

Assay to Proof Structural Integrity of Human IgG in a Sample from an Experimental Animal Biotinylated antibody M-1.19.31 can be bound to streptavidin-coated microtiter plates (SA-MTP) in the first step. The excess of unbound antibody can be removed by washing. Samples/standards, e.g. anti-IL13Rα1 antibody, spiked in cynomolgus serum can be added to the plate and incubated for 60 min. at ambient temperature, with shaking. After having washed away unbound antibodies, 100 µl digoxygenylated antibody M-1.3.2 can be added to the plate. After washing, the bound digoxygenylated antibodies can be detected with an anti-digoxygenin antibody-HRP conjugate. Absorbance values of each serum sample can be determined in triplicates.

EXAMPLE 9

Assay for Quantification of Human Antibodies (Human IgG) in a Sample from an Experimental Animal Using a Fc-Fusion Protein (Antigen) in Combination with Anti-Human IgG Antibody According to the Invention The biotinylated antigen (Bi-X) was bound to streptavidin-coated microtiter plates (SA-MTP) in the first step. The excess of unbound antigen was removed by washing. Afterwards anti-X antibody spiked in cynomolgus serum was bound to the immobilized human receptor X. After washing away unbound substances, the bound anti-X antibody was detected with digoxygenylated monoclonal antibody against human Fab fragment (antibody M-1.19.31) followed by incubation with a horse-radish peroxidase labeled anti-digoxigenin antibody. Absorbance values of each serum sample are determined in triplicates.

TABLE 2

OD data.

| ng/ml | OD405 nm |
|---|---|
| 50.00 | 2.006 |
| 25.00 | 1.203 |
| 12.50 | 0.662 |
| 6.25 | 0.350 |
| 3.13 | 0.188 |
| 1.56 | 0.107 |
| 0.78 | 0.071 |
| 0 | 0.034 |

EXAMPLE 10

Dot Blot—Conformation Vs. Linear Epitope

To determine, whether the anti-human IgG antibodies detect a conformation epitope or a linear epitope, a dot-blot analytic was performed.

During this test, the antigen-protein (human IgG) was dotted to a nitrocellulose membrane in a native and a denaturized form. To receive the denaturized form, the antigen-protein was incubated with SDS on a shaker at 37° C. over night. Both forms were dotted in a concentration series to the membrane. After complete drying of the membrane, the surface was blocked with a blocking buffer (Roti-Block, Roth, Germany) for 60 min. at ambient temperature with shaking. After washing of the membrane, it was incubated with a solution containing digoxygenylated antibody M-1.19.31. After washing, the bound digoxygenylated antibody was detected with an anti-digoxigenin antibody-HRP conjugate. The HRP of the antibody-enzyme conjugates catalyzes the color reaction of BM-Blue substrate. The signal can directly be controlled visually and captured with a scanner.

EXAMPLE 11

Assessment of Antibody Binding/Specificity by ELISA

To determine which kind of Human IgG subclass is bound by the researched anti human antibodies, a bridging ELISA analytic was performed.

Biotinylated antibodies M-R10Z8E9, M-1.3.2, M-1.5.8, M-1.7.10 and M-1.19.31 were bound to the streptavidin microtiterplate in the first step. In a second step, human IgG antibodies of different subclasses were incubated. Human IgG1 kappa; human IgG1 lambda; human IgG4; chimeric human IgG1; human IgG2 (polyclonal purified human IgG2) and human IgG3 (polyclonal purified human IgG3) were prepared in a dilution series and incubated to the streptavidin microtiterplate, coated with biotinylated anti human antibody. After a washing step, the same antibodies as used for coating were used as detection antibodies in digoxygenylated form. This means that the same anti human antibody clone was used for coating and detection. For example one plate was coated with M-1.7.10 Bi and M-1.7.10-Dig was used for detection. After incubation and a washing step, this step was followed by incubation with a horse-radish peroxidase labeled anti-digoxygenin antibody. Absorbance values of each serum sample have been determined in triplicates.

TABLE 3

Resume of bridging ELISA analytics

| | Antibody used for coating/detection | | | | |
|---|---|---|---|---|---|
| Sample | mAb M-R10Z8E9 | mAb M-1.3.2 | mAb M-1.5.8 | mAb M-1.7.10 | mAb M-1.19.31 |
| IgG1-kappa | ++ | ++ | ++ | ++ | ++ |
| IgG1-Lambda | ++ | -- | -- | -- | ++ |
| IgG4 | ++ | + | + | ++ | -- |
| Chimeric IgG1 | ++ | + | + | ++ | ++ |
| IgG2 | + | +- | +- | ++ | -- |
| IgG3 | +- | -- | -- | -- | -- |
| IgG1-kappa Fab | -- | ++ | ++ | ++ | ++ |
| IgG1-Lambda Fab | -- | -- | -- | -- | + |

++ Highly positive
+ Positive
+- Weak signal
-- Negative

EXAMPLE 12

Epitope Characterization of Antibody Against Antibody of Human IgG1 Class Based on Cross-Competition by Utilizing SPR Instrument: BIACORE® T100
Chip: CM5 (BIAcore BR-1006-68)
Coupling: amine coupling
Buffer: PBS (BIAcore BR-1006-72), pH 7.4, 25° C.

For epitope binning assays via cross-competition, a high amount of anti mouse Fcγ antibody (from goat, Jackson Immuno Research Cat. No. 115-005-071) is coupled to sensor chip surface for presentation of the anti-human-IgG antibody. (approx. 8,000-12,000 RU). After injection of 10 µg/ml of the first anti-human-IgG antibody, residual free binding capacities of capture anti mouse antibody is saturated with 250 µg/ml mouse immunoglobulins. After blocking of free anti mouse binding sites, a human Fab fragment is injected at a concentration of 10 µg/ml for 1 min. and will be bound by the first anti-human-IgG antibody. The second anti-human-IgG antibody is injected at a concentration of 10 µg/ml for 1 min. In case of different binding sites of the first and second antibody, the second antibody will be able to bind to the immobilized human Fab fragment. Identical binding sites will lead to no binding of the second antihuman-IgG antibody. Positivity of the second binding is defined by a cut-point of 10 RU binding. After each cycle, the sensor chip is regenerated by injection of 100 mM $H_3PO_4$, to remove the bound immune complex. Only the covalent coupled anti mouse antibody will remain bound to the chip.

By analyzing all possible combinations of anti human antibodies, epitope groups can be defined.

TABLE 4

Results of BIAcore binning assay (Responses in RU)

| First anti human IgG | Second anti human IgG | | | |
|---|---|---|---|---|
| | mAb M-1.3.2 | mAb M-1.5.8 | mAb M-1.7.10 | mAb M-1.19.31 |
| mAb M-1.3.2 | −3.6 | −2.1 | 32.1 | 18.4 |
| mAb M-1.5.8 | −4.1 | −3.1 | 28.5 | 15.5 |
| mAb M-1.7.10 | 93.5 | 80.8 | 4.4 | 23.8 |
| mAb M-1.19.31 | 183.7 | 165.9 | 114.0 | −2.3 |

TABLE 5

Resulting epitope groups
Epitope Groups:

| 1 | mAb<HuIgG>M-1.7.10 |
|---|---|
| 2 | mAb<HuIgG>M-1.3.2/1.5.8 |
| 3 | mAb<HuIgG>M-1.19.31 |

What is claimed:

1. A monoclonal antibody produced by the hybridoma cell line DSM ACC3076.

2. The monoclonal antibody of claim 1, wherein the monoclonal antibody specifically binds to an antibody of human IgG1 class.

3. The monoclonal antibody of claim 1, wherein the monoclonal antibody does not specifically bind to an immunoglobulin of rhesus monkey, marmoset monkey, baboon monkey, or cynomolgus monkey.

4. The monoclonal antibody of claim 1, wherein the monoclonal antibody binds to an antibody of human IgG1 class having a kappa light chain.

5. The monoclonal antibody of claim 1, wherein the monoclonal antibody binds to an antibody of human IgG1 class having a lambda light chain.

6. The monoclonal antibody of claim 1, wherein the monoclonal antibody does not bind to an antibody of human IgG2 class, human IgG3 class, or human IgG4 class.

7. The monoclonal antibody of claim 1, wherein the monoclonal antibody binds to the Fab of an antibody of human IgG1 class having a kappa light chain.

8. The monoclonal antibody of claim 1, wherein the monoclonal antibody binds to the Fab of an antibody of human IgG1 class having a lambda light chain.

9. The monoclonal antibody of claim 1, wherein the epitope comprises amino acid residues 16, 82, and 97 of SEQ ID NO:04.

10. The hybridoma cell line DSM ACC3076.

11. A kit comprising
a) an isolated monoclonal antibody produced by the hybridoma cell line DSM ACC3006, or produced by the hybridoma cell line DSM ACC 3007, or produced by the hybridoma cell line DSM ACC3008, or produced by the hybridoma cell line DSM ACC3076 for use in an immunoassay as capture reagent, and
b) an isolated monoclonal antibody produced by the hybridoma cell line DSM ACC3006, or produced by the hybridoma cell line DSM ACC 3007, or produced by the hybridoma cell line DSM ACC3008, or produced by the hybridoma cell line DSM ACC3076 for use in an immunoassay as detection reagent.

12. An antibody composition comprising a monoclonal antibody produced by the hybridoma cell line DSM ACC3076, and comprising one or more monoclonal antibodies selected from the group consisting of a monoclonal antibody produced by the hybridoma cell line DSM ACC3006, a monoclonal antibody produced by the hybridoma cell line DSM ACC3007, a monoclonal antibody produced by the hybridoma cell line DSM ACC3008, and a monoclonal antibody produced by the hybridoma the cell line DSM ACC2708.

13. A method for detecting the presence of a therapeutic antibody of human IgG1 class in a sample obtained from an experimental animal, the method comprising
a) obtaining a sample to be analyzed from the experimental animal,
b) incubating the sample with a capture antibody, wherein the capture antibody is selected from the group consisting of the monoclonal antibody produced by the hybridoma cell line DSM ACC3006, the monoclonal antibody produced by the hybridoma cell line DSM ACC3007, the monoclonal antibody produced by hybridoma cell line DSM ACC3008, and the monoclonal antibody produced by the hybridoma cell line DSM ACC2708, thereby forming a complex comprising the antibody of human IgG1 class and the capture antibody,
c) incubating the complex of the human antibody of IgG1 class and the capture antibody with a detection antibody, wherein the detection antibody is the monoclonal antibody of claim 1, thereby forming a second complex comprising the antibody of human IgG1 class, the capture antibody, and the detection antibody, and d) detecting the second complex, wherein the detection of the second complex correlates to the presence of the antibody of human IgG1 class, thereby detecting the presence of a therapeutic antibody of human IgG1 class in a sample obtained from an experimental animal.

14. The method of claim 13, wherein detecting the second complex is by direct detection or by indirect detection.

15. A method for detecting the presence of a therapeutic antibody of human IgG1 class in a sample obtained from an experimental animal, the method comprising
   a) obtaining a sample to be analyzed from the experimental animal,
   b) incubating the sample with a capture antibody, wherein the capture antibody is the monoclonal antibody of claim 1, thereby forming a complex comprising the antibody of human IgG1 class and the capture antibody,
   c) incubating the complex of the antibody of human IgG1 class and the capture antibody with a detection antibody, wherein the detection antibody is selected from the group consisting of the monoclonal antibody produced by the hybridoma cell line DSM ACC3006, the monoclonal antibody produced by the hybridoma cell line DSM ACC3007, the monoclonal antibody produced by hybridoma cell line DSM ACC3008, and the monoclonal antibody produced by the hybridoma cell line DSM ACC2708, thereby forming a second complex comprising the antibody of human IgG1 class, the capture antibody, and the detection antibody, and
   d) detecting the second complex, wherein the detection of the second complex correlates to the presence of the antibody of human IgG1 class, thereby detecting the presence of a therapeutic antibody of human IgG1 class in a sample obtained from an experimental animal.

16. The method of claim 15, wherein detecting the second complex is by direct detection or by indirect detection.

17. A method for detecting the presence of a therapeutic antibody of human IgG1 class in a sample obtained from an experimental animal, the method comprising
   a) obtaining a sample to be analyzed from the experimental animal,
   b) incubating a biotinylated capture antibody to a streptavidin-coated microtiter plate, wherein the capture antibody is selected from the group consisting of the monoclonal antibody obtained from the hybridoma cell line DSM ACC3006, the hybridoma cell line DSM ACC3007, the hybridoma cell line DSM ACC3008, or the hybridoma cell line DSM ACC2708,
   c) adding the sample to be analyzed to the microtiter plate, thereby forming a complex of the antibody of human IgG1 class and the biotinylated capture antibody bound to the streptavidin-coated microtiter plate,
   d) incubating the complex in the microtiter plate with a detection antibody, thereby forming a second complex, wherein the second complex comprises the antibody of human IgG1 class, the biotinylated capture antibody, and the detection antibody, wherein the detection antibody is the monoclonal antibody of claim 1, and
   e) detecting the second complex, wherein the detection of the second complex correlates to the presence of the antibody of human IgG1 class, thereby detecting the presence of a therapeutic antibody of human IgG1 class in a sample obtained from an experimental animal.

18. The method of claim 17, wherein detecting the second complex is by direct detection or by indirect detection.

19. The method of claim 17, wherein the detection antibody is digoxygenylated.

20. The method of claim 19, wherein the detecting is performed using a horseradish peroxidase labeled anti-digoxygenin antibody.

21. A method for detecting the presence of a therapeutic antibody of human IgG1 class in a sample obtained from an experimental animal, the method comprising
   a) obtaining a sample to be analyzed from the experimental animal,
   b) incubating a biotinylated capture antibody to a streptavidin-coated microtiter plate, wherein the capture antibody is the monoclonal antibody of claim 1,
   c) adding the sample to be analyzed to the microtiter plate, thereby forming a complex of the antibody of human IgG1 class and the biotinylated capture antibody bound to the streptavidin-coated microtiter plate,
   d) incubating the complex in the microtiter plate with a detection antibody, thereby forming a second complex, wherein the second complex comprises the antibody of human IgG1 class, the biotinylated capture antibody, and the detection antibody, wherein the detection antibody is the monoclonal antibody selected from the group consisting of the monoclonal antibody obtained from the hybridoma cell line DSM ACC3006, the hybridoma cell line DSM ACC3007, the hybridoma cell line DSM ACC3008, or the hybridoma cell line DSM ACC2708, and
   e) detecting the second complex, wherein the detection of the second complex correlates to the presence of the antibody of human IgG1 class, thereby detecting the presence of a therapeutic antibody of human IgG1 class in a sample obtained from an experimental animal.

22. The method of claim 21, wherein detecting the second complex is by direct detection or by indirect detection.

23. The method of claim 21, wherein the detection antibody is digoxygenylated.

24. The method of claim 23, wherein the detecting is performed using a horseradish peroxidase labeled anti-digoxygenin antibody.

25. The method of claim 13, claim 15, claim 17, or claim 21, characterized in that the therapeutic antibody is a Fab.

26. The method of claim 13, claim 15, claim 17, or claim 21, wherein the experimental animal is selected from the group comprising the members of the families of marmosets and tamarins, old world monkeys, dwarf and mouse lemurs, gibbons and lesser apes, true lemurs, as well as crossings thereof.

* * * * *